United States Patent
Stevens et al.

[11] Patent Number: 6,155,117
[45] Date of Patent: Dec. 5, 2000

[54] EDGE DETECTION AND SEAM TRACKING WITH EMATS

[75] Inventors: Donald M. Stevens, Lovingston; Daniel T. MacLauchlan, Lynchburg, both of Va.; Paul J. Berbakov, Norton, Ohio

[73] Assignee: McDermott Technology, Inc., New Orleans, La.

[21] Appl. No.: 09/271,742

[22] Filed: Mar. 18, 1999

[51] Int. Cl.$^7$ .................................................. G01N 29/18
[52] U.S. Cl. ............................................. 73/643; 228/104
[58] Field of Search ........................... 73/643, 597, 629; 228/56.5, 104

[56] References Cited

U.S. PATENT DOCUMENTS

| | | | |
|---|---|---|---|
| 4,588,873 | 5/1986 | Fenn et al. | 219/124.34 |
| 5,237,874 | 8/1993 | Latimer et al. | 73/643 |
| 5,439,157 | 8/1995 | Geier et al. | 228/9 |
| 5,537,876 | 7/1996 | Davidson et al. | 73/643 |

*Primary Examiner*—John E. Chapman
*Attorney, Agent, or Firm*—R. J. Edwards; Eric Marich; R. C. Baraona

[57] ABSTRACT

A method for detecting the location of an edge, interface, seam or other structure of a workpiece uses one or two electromagnetic acoustic transducers (EMATs) to transmit an ultrasonic wave along the workpiece toward the edge and to receive a reflected wave. The velocity of the wave in the material is used in conjunction with the round trip time-of-flight (TOF) of the transmitted and reflected wave, to calculate the location of the edge. This is done by placing the transducer or transducers at known locations on the workpiece. A surface wave or 90 degree shear wave can be utilized and no contact is needed between the transducer and the surface of the workpiece. Rough and/or dirty surfaces and hostile environments can be accommodated while practicing the invention.

12 Claims, 5 Drawing Sheets

D1= (TOF(SENSOR1)/2) X VELOCITY

D2= (TOF(SENSOR2)/2) X VELOCITY

D1 = (TOF(SENSOR1)/2) X VELOCITY

D2 = (TOF(SENSOR2)/2) X VELOCITY

D1 = (TOF 1)/2) X VELOCITY
D2 = (TOF 2)/2) X VELOCITY

D1= (TOF(SENSOR1)/2 X) VELOCITY
D2= (TOF(SENSOR2)/2 X) VELOCITY

EDGE DETECTION AND SEAM TRACKING WITH EMATS

FIELD AND BACKGROUND OF THE INVENTION

The present invention relates in general to he sensing of edges in various industrial processes and, in particular, to a new and useful method and apparatus for measuring the distance to an edge, seam, or interface of a workpiece, and which uses one or two EMATs.

It is known to use an electromagnetic acoustic transducer (EMAT) to inspect a weld. U.S. Pat. No. 5,439,157 to Geier et al. describes an automated butt weld inspection system which employs an EMAT to generate shear horizontal (SH) waves for detecting defects in butt welds. In accomplishing that task, the commercial embodiment of that system, known as a TEMATE® inspection system, employs an inductive proximity sensor to detect the presence of the edge of the steel plate. More particularly, the proximity sensor is used by sensing when the steel plate is under the proximity sensor, scanning towards the edge of the plate, and sensing the point at which the steel is no longer present to indicate the edge of the plate. The location of the edge using such an inductive proximity sensor typically requires several seconds, and its accuracy is somewhat limited, albeit sufficient for the system disclosed in the '157 patent.

Reflected ultrasound has also been used to automatically control the production of a weld seam. U.S. Pat. No. 4,588,873 to Fenn et al. describes the detection of weld seams, material edges, and the molten weld pool interface using conventional ultrasonic test methods for the purpose of controlling the welding process. Specifically, it describes the use of conventional ultrasonic surface waves for weld seam detection and tracking.

One advantage which EMATs possess over all other ultrasonic sensing techniques is the fact that EMATs do not require couplants or gels between the EMAT sensor and a surface of the workpiece under inspection.

Detection of the edge of a material during welding or other processing is often a necessary and integral part of the process. For instance, during automatic welding, tracking of the seam between the two components being welded is necessary for proper execution of the process. Other processes, such as steel forming and cutting, require accurate location of the work piece edges during the process.

Currently, edge or seam tracking is usually performed with the aid of a laser or by other optical methods. A light beam is transmitted to the part. If the beam strikes the component, there is a return beam. If the beam passes by the edge or seam, there is no return beam. Multiple beams may be used to provide full coverage of the area in which the seam or edge is located; alternatively, a beam may be swept across the area to locate the edge or seam, indicated by the change in the returned beam. These optical methods must provide precise measurements of the edge location, typically +/−0.010" or better, in a process environment that may include welding, cutting, or grinding. Maintaining a clean and clear optical path in this environment is often difficult. In addition, the surface finish of the material dictates the quality of the reflected beam. In some cases, a rough surface may scatter the beam and not allow a strong enough signal to be returned. In other cases, a very smooth surface may provide a beam reflection that is difficult to process due to beam strength or beam scattering.

A need remains for a convenient and effective technique for determining the position of an edge or seam for use in various welding, metal cutting, and other processes.

SUMMARY OF THE INVENTION

An EMAT, generating ultrasonic waves, can be used to detect edges, seams, or interfaces on a workpiece. The EMAT generates surface waves that propagate on the surface of the workpiece until they reach an edge, seam, or interface at which point they are reflected and can be detected by the original EMAT sensor which generated the surface waves, or by a companion (receiving) EMAT sensor. By measuring the time-of-flight (TOF) of the surface waves, and knowing the velocity of the surface waves in the material from which the workpiece is made, the distance to the edge, seam, or interface can be calculated.

Accordingly, one aspect of the present invention is drawn to a method for detecting the location of an edge on a workpiece. The steps of this method comprise: positioning electromagnetic acoustic transducer (EMAT) sensor means at a known location adjacent the workpiece, using the EMAT sensor means to gent rate an ultrasonic wave along a surface of the workpiece toward the edge, and detecting a reflected ultrasonic wave from the edge; measuring a round trip time-of-flight (TOF) of the ultrasonic wave to propagate from the EMAT sensor means to the edge, be reflected from the edge, and propagate back to the EMAT sensor means; and, knowing a velocity of the ultrasonic wave in the workpiece, calculating the distance from the EMAT sensor means to the edge using the TOF and the velocity to determine the location of the edge on the workpiece as a function of the known location of the EMAT sensor means.

The EMAT sensor means can be used to determine the position of an edge in the form of a seam in the workpiece. The EMAT sensor means produces an ultrasonic surface wave which emanates from the EMAT sensor means in a straight line of known orientation. This property can be used to determine whether an edge of a workpiece is perpendicular to the EMAT sensor means; i.e., perpendicular to the direction of propagation of the ultrasonic surface wave. Thus, another aspect of the invent on is drawn to a method for determining whether an edge of a workpiece is perpendicular o another line. The steps of this method comprise: positioning electromagnetic acoustic transducer (EMAT) sensor means at a known location adjacent the workpiece and using the EMAT sensor means to generate an ultrasonic wave along a surface of the workpiece in a straight line of known orientation. An amplitude of a received ultrasonic wave which has been reflected from the edge and received back at the EMAT sensor means is measured while rotating the EMAT sensor means about a central axis of the EMAT sensor means. Finally, the method involves determining at what angular position the maximum amplitude of the received ultrasonic wave that has been reflected from the edge is obtained, thereby indicating when the ultrasonic beam produced by the EMAT sensor means is perpendicular to the edge.

The present invention can accommodate surface roughness, dirt, grease or other debris, as well as harsh environmental conditions, while still producing an accurate determination of the location of the edge, seam, or other type of interface of the workpiece. The method of the present invention employs components which are simple in design, rugged in construction, and economical to manufacture.

The various features of novelty which characterize the invention are pointed out with particularity in the claims annexed to and forming a part of this disclosure. For a better understanding of the invention, its operating advantages and specific benefits attained by its uses, reference is made to the accompanying drawings and descriptive matter in which a preferred embodiment of the invention is illustrated.

DESCRIPTION OF THE PREFERRED EMBODIMENTS

Figure 1:
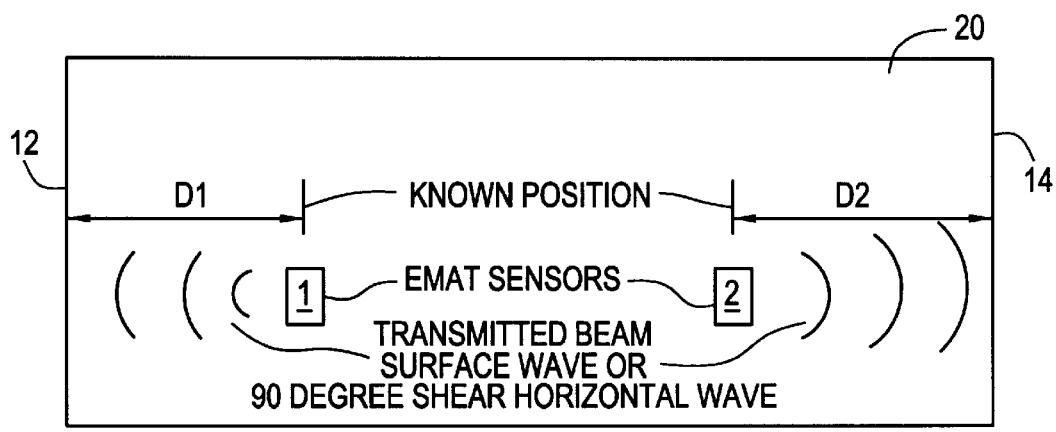
FIG. 1 is a plan view of a workpiece with a pair of edges whose locations are to be detected according to the present invention.

Referring to the drawings generally, wherein like reference numerals designate the same or functionally similar elements throughout the several drawings, the invention embodied therein comprises a method for detecting an edge of a workpiece. As used herein, the term edge will be used to refer to edges, seams, or other interfaces in a workpiece which are capable of reflecting ultrasonic waves.

An electromagnetic acoustic transducer (EMAT) sensor, generating ultrasonic waves, is used to detect these edges, seams, or interface. The EMAT sensor generates surface waves that propagate on the surface of the material until they reach an edge or seam. At this interface, the ultrasonic beam is reflected and is detected by the original or a companion sensor. By measuring the round trip time-of-flight (TOF) of the ultrasonic wave to propagate from the EMAT sensor means to the edge, be reflected from the edge, and propagate back to the EMAT sensor means, and knowing the velocity of the surface wave in the workpiece (which is a function of the type of material from which the workpiece is made), the distance from the EMAT sensor means to the edge or seam can be calculated. Since the location of the EMAT sensor is known, the location of the edge can be determined quite accurately—within a few thousandths of an inch. Alternatively, an EMAT sensor generating a 90 degree shear horizontal wave may also be used. This type of ultrasonic wave propagates just under the material surface and is not strongly influenced by the surface finish.

Figure 2:
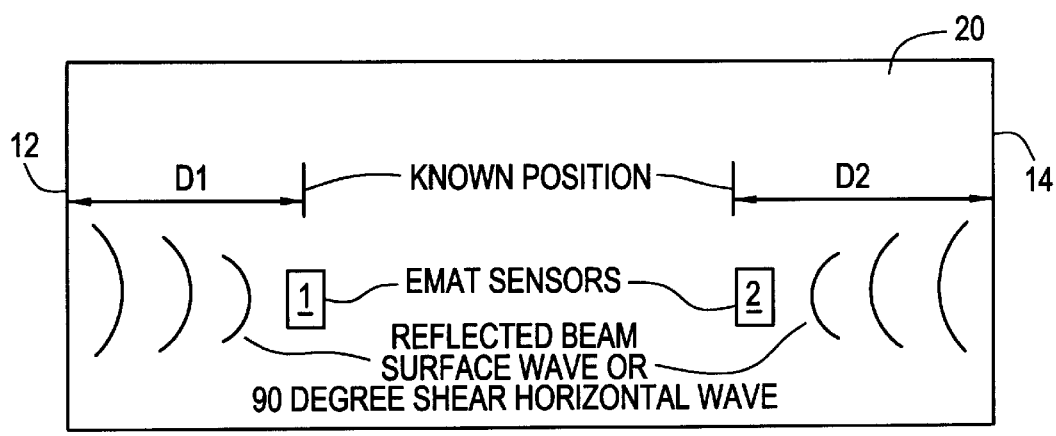
FIG. 2 is a view similar to FIG. 1 illustrating the path of returning reflected beams from the edges.

Examples of applications of the invention are illustrated in the Figures forming a part of the present disclosure. FIGS. 1 and 2 show the use of two EMAT sensors 1 and 2 to measure the location of edges 12, 14 of a plate or workpiece 20. The location of each of the EMAT sensors 1, 2 is known. Each EMAT sensor 1, 2 transmits a surface or 90 degree ultrasonic shear horizontal wave toward the component edge. After being reflected back from the edge 12 or 14, each EMAT sensor 1, 2 then detects the returning ultrasonic wave. The surface wave or shear wave velocity of the plate can be measured and defined beforehand. The round trip time-of-flight (TOF) of the ultrasonic wave to propagate from either EMAT sensor 1, 2 to its respective edge 12, 14, be reflected therefrom, and propagate back to the EMAT sensor 1, 2 is accurately measured. The distances D1 and D2 to the edge from the known positions of each of the EMAT sensors 1, 2 can then be calculated as follows: (D1=(TOF EMAT sensor 1)/2×velocity) and (D2=TOF EMAT sensor 2)/2×velocity). For detecting the reflected ultrasonic wave, the original transmitting EMAT sensor 1, 2 may be used or separate receiving EMAT sensors that overlay (lie on top of) each of the transmitting EMAT sensors 1, 2 may be used.

Figure 3:
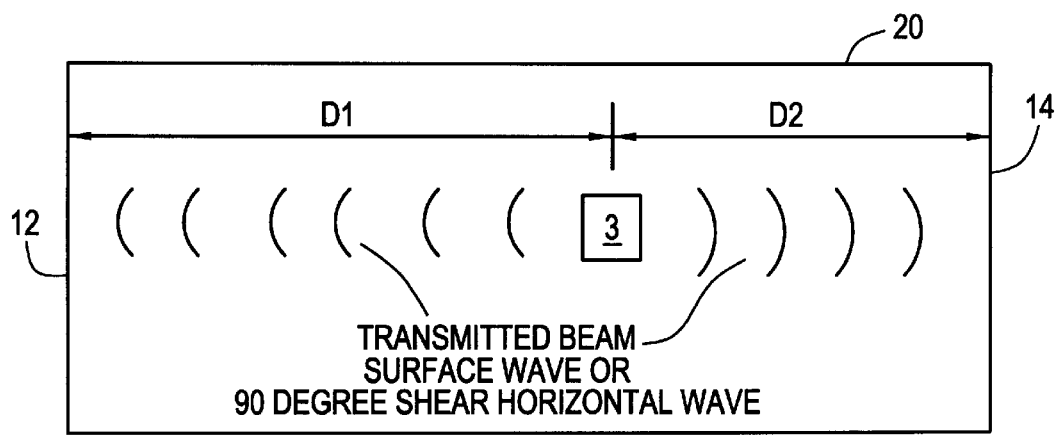
FIG. 3 is a view similar to FIG. 1 of a further embodiment of the present invention.
Figure 4:
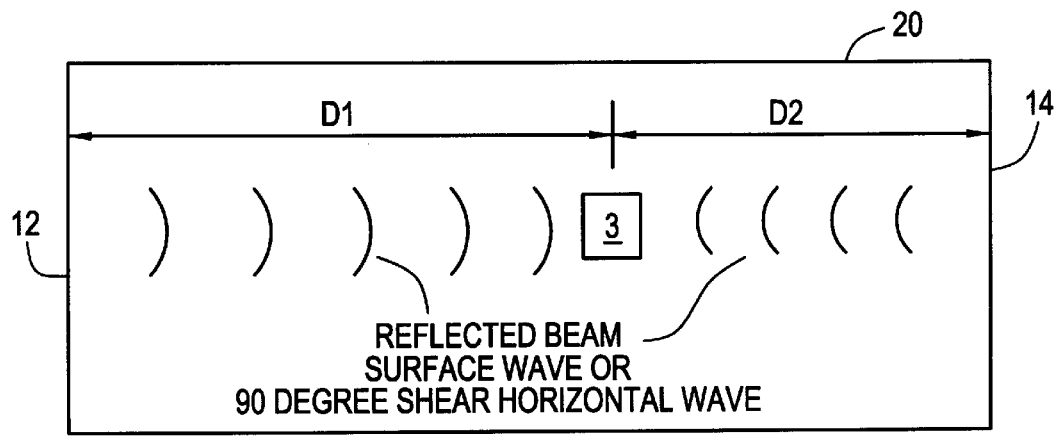
FIG. 4 is a view similar to FIG. 2 of the further embodiment of the present invention.

FIGS. 3 and 4 show the use of one EMAT sensor 3 to measure the location of both edges 12, 14. Because EMATs are bi-directional, they are capable of generating an ultrasonic wave that propagates in opposite directions. In this application, the EMAT sensor 3 must be closer to one edge than the other or else the TOF to both edges would be identical. The position of the EMAT sensor 3 is known. The EMAT sensor 3 transmits an ultrasonic wave that propagates in both directions. At the edges 12, 14, the ultrasonic waves are reflected. The EMAT sensor 3 then detects the reflected waves. Each round trip TOF is again accurately measured and the distances the two edges 12, 14 are calculated in similar fashion as before; i.e., (D1=(TOF1)/2×velocity; D2=(TOF2)/2×velocity).

Figure 5:
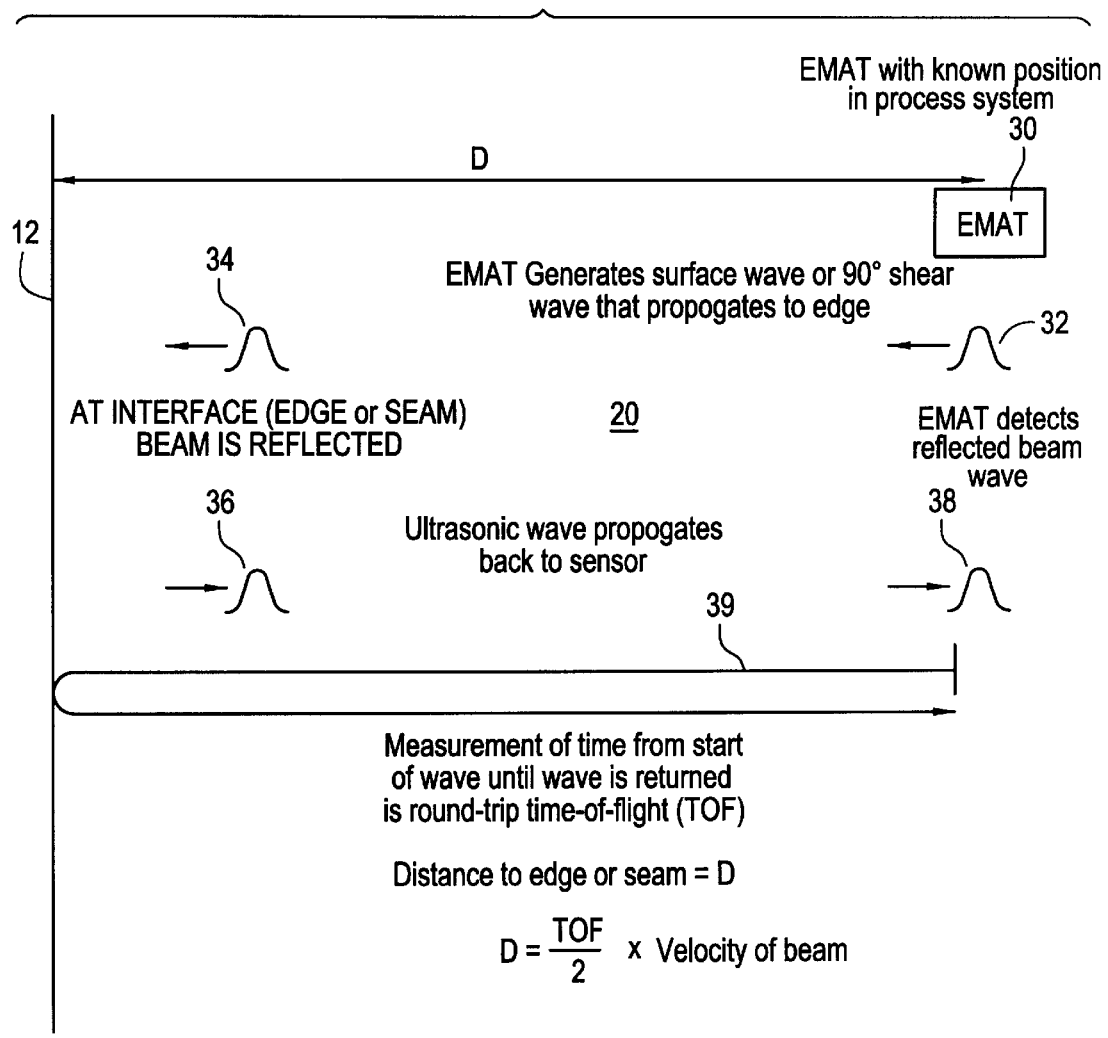
FIG. 5 is a schematic illustration further explaining the method of the present invention.

FIG. 5 provides another perspective on the measurement of the time-of-flight (TOF) and the calculation of the required distance, D. As shown in FIG. 5, an EMAT sensor 30 at a known distance from an edge 12 can generate an EMAT surface wave, or 90 degree shear wave, that propagates from the EMAT sensor position 32 toward the edge at 34. At the edge or other interface, the wave is reflected as shown at 36, and this ultrasonic wave propagates back and is detected at 38, at the sending EMAT sensor 30 or at a separately provided receiving EMAT sensor, as described before, and collectively both embodiments are here referred to as EMAT sensor means.

The round trip TOF is shown at 39 and equals ½ the time-of-flight times the velocity of the beam which can be measured for the material carrying the edge 12.

Figure 6:
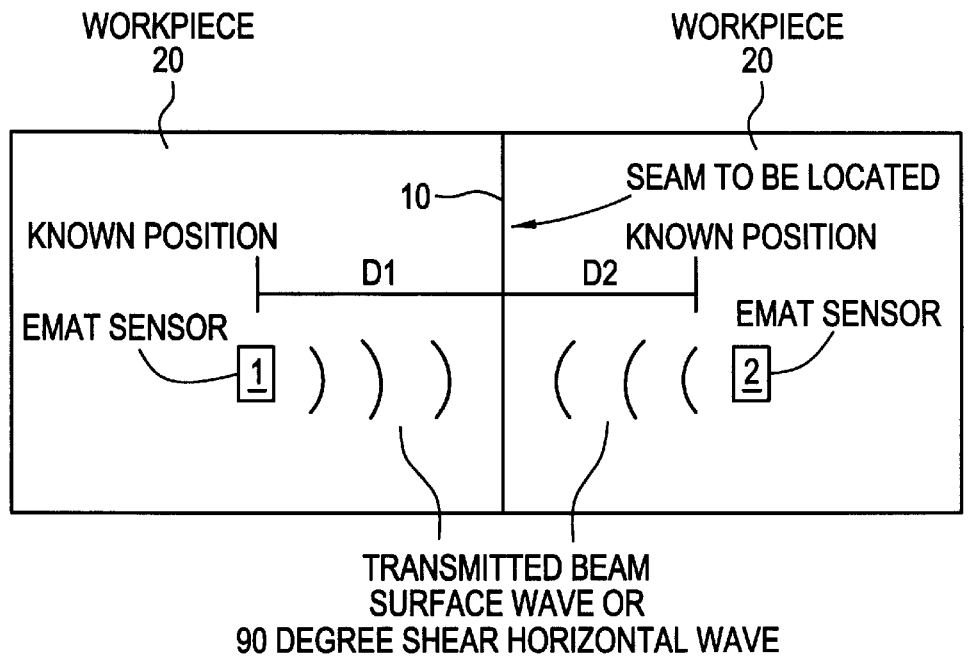
FIG. 6 is a view similar to FIG. 1 showing use of the present invention to detect a seam.
Figure 7:
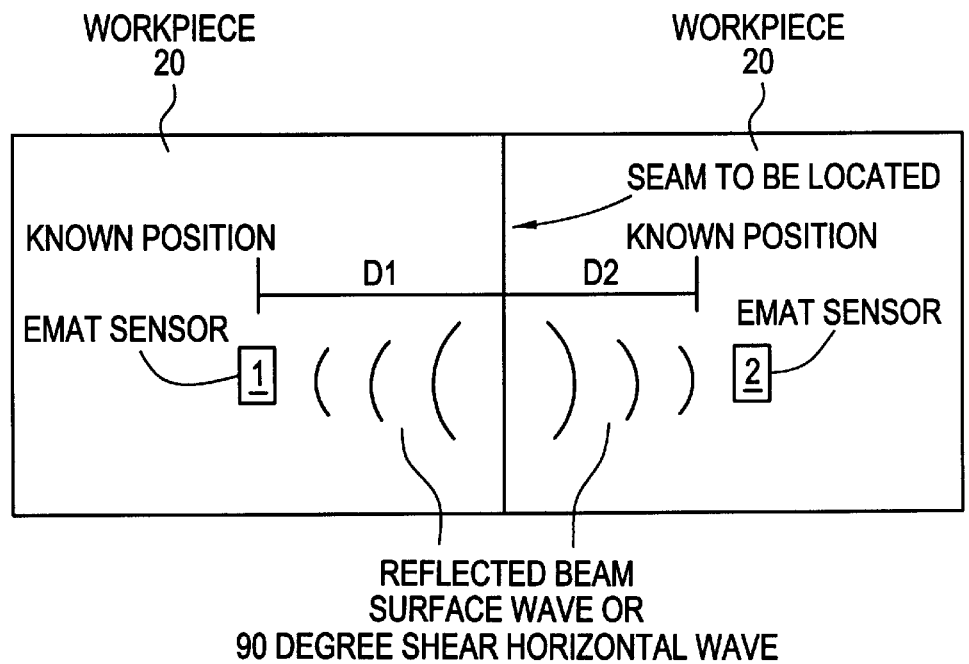
FIG. 7 is a view similar to FIG. 2 illustrating the method of detecting the seam.

FIGS. 6 and 7 show a typical sensor configuration for applications such as seam tracking during automatic welding. In this case, the EMAT sensors' positions are known relative to the process, such as a welding head. The seam 10 is located between the two EMAT sensors 1 and 2. Each EMAT sensor transmits an ultrasonic wave that propagates to the seam 10. This may be a surface wave or a 90 degree shear wave. At the seam 10, the ultrasonic wave is reflected and propagates back to the EMAT sensors. The reflected wave may be detected with the transmitting EMAT sensor or with a receiving EMAT sensor that overlays the transmitting sensor. The velocity of the ultrasonic wave in the material being welded is known. The round trip time-of-flight (TOF) is measured and the distances from each EMAT sensor to the seam 10 can be calculated. Since the EMAT sensor positions are known, the seam 10 is located.

In all of the above cases, the EMAT sensor or sensors may be mounted on a movable platform with rollers or wheels which would allow relative movement between the EMAT sensors and the workpiece during the process. Since EMATs do not require a liquid to couple to the material, there may even be a small air gap between the EMAT sensor(s) and the material and no physical contact is required. This is advantageous when the workpiece is at an elevated temperature. The use of EMATs for edge detection and/or seam tracking according to the present invention solves the following problems:

1. Optical methods using lasers or light beams must have a clear path to the surface of the workpiece. In contrast, using EMAT sensors according to the present invention only requires the EMAT sensors to be located in proximity to the surface of the workpiece, thereby minimizing environmental effects on the EMAT performance.

2. The surface finish of a workpiece (either too dirty or shiny), can impact laser and light-based detection systems. Surface finish does not impact the EMAT performance. The surface wave mode is relatively insensitive to dirt or other loose foreign material on the workpiece surface. The 90 degree shear wave is also insensitive to surface irregularities in the material itself, such as reinforcements, abrupt changes in thickness, etc.

3. Conventional piezoelectric ultrasonics require liquid couplants that may be incompatible with the process, such as high temperature cutting or welding, and usually cannot be used since surface wave generation is difficult.

4. Conventional piezoelectric ultrasonics cannot generate 90 degree shear horizontal waves in a practical manner.

5. EMATs can operate at temperatures of 1,200 degrees F. or above. Conventional piezoelectric ultrasonic sensors typically only work at temperatures up to about 190 degrees F. for scanning applications; their upper temperature limit is actually determined by the temperature handling capability of the couplants used.

Figure 8:
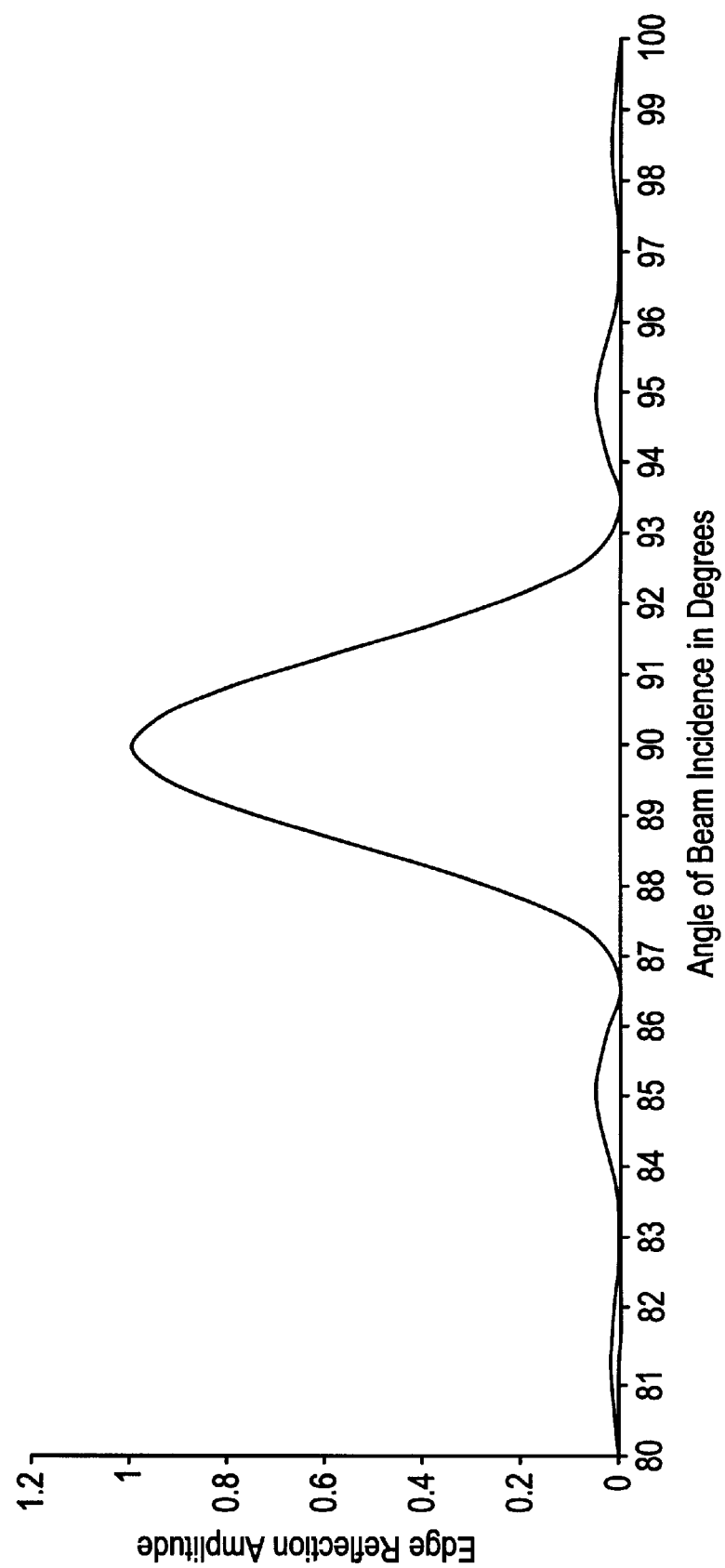
FIG. 8 is a graph of the expected reflected signal amplitude for an edge signal as a function of beam angle of incidence.

6. The present EMAT sensor approach can also be used to determine if the workpiece edge is perpendicular to the sensor, since the amplitude of the received ultrasonic wave is very dependent on the alignment between the EMAT sensor and the edge. FIG. 8 illustrates this dependency and how amplitude varies with the angle of beam incidence. If the edge is not perpendicular, the amplitude is smaller than when the edge is exactly perpendicular. This feature can be used to establish precise alignment of the edge as may be required in cutting or welding operations.

Advantages of the present invention include:

1. EMATs do not require a clear light path to the component or workpiece, and thus EMAT performance is not impacted by a dusty or dirty environment that would impact the performance of a laser or light based system.

2. The EMAT approach can work at high temperatures where conventional piezoelectric ultrasonic sensors car not operate.

3. The EMAT does not require a liquid couplant that is required with conventional ultrasonics.

4. The EMAT can generate surface waves that are difficult to generate with conventional ultrasonics.

5. The EMAT can generate 90 degree shear horizontal waves that cannot be generated with conventional ultrasonics in a practical manner.

6. The EMAT performance is not impacted by dirt or other loose foreign material on the component surface which can affect the performance of laser or light based systems.

7. EMAT measurements are not affected by bright, shiny edges which sometimes result in incorrect performance of light or laser based systems, and the surface finish of the material does not impact the performance of the EMAT sensor, especially the 90 degree shear horizontal wave sensor. Even the surface wave mode sensor can tolerate some level of surface roughness.

U.S. Pat. No. 5,439,157 to Geier et al. describes the use of EMAT generated shear horizontal (SH) waves for the detection of defects, in butt welds. It does not describe edge detection using EMATs. The edge detection approach used in that invention relies on an inductive proximity sensor that detects the presence of the edge of, e.g. steel plate by sensing when the steel plate is under the proximity sensor, scanning towards the edge of the plate, and sensing the point at which the steel is no longer present to indicate the edge of the plate. This edge detection method does not require scanning a sensor over the edge of the plate in order to detect it. The edge location is determined from an ultrasonic time of flight measurement. The location of the edge can be ascertained in less than $\frac{1}{100}^{th}$ of a second from time of flight (TOF) measurements in most cases, as opposed to several seconds needed to scan over the edge with a proximity sensor. The accuracy of edge location using ultrasonic time of flight is typically much greater than for a proximity sensor scanning over the edge of a plate.

U.S. Pat. No. 4,588,873 to Fenn et al. describes the detection of weld seams, material edges, and the molten weld pool interface using conventional ultrasonic test methods for the purpose of controlling the welding process. Specifically, it describes the use of conventional ultrasonic surface waves for weld seam detection and tracking. The EMAT surface (Rayleigh) wave approach generates surface waves that do not require a couplant gel or liquid. This enables high temperature testing, allows reliable rapid scanning, and improves accuracy by eliminating couplant path related errors. Use of EMATs for weld seam tracking is very different than for edge detection. The present invention also uses surface skimming, shear horizontal waves for weld seam tracking and edge detection. These waves cannot be practically generated using conventional ultrasonic transducers for scanning applications. They have the advantage over surface waves of being insensitive to liquids on the surface of the metal, and less sensitive to surface conditions, such as roughness, as described above. In addition, since they are surface skimming, they do not require reflecting off of the back surface of the material as do the shear waves described in U.S. Pat. No. 4,588,873 to Fenn et al. Variations in material thickness would create errors in the location of the edge using the shear waves as described in the '873 patent.

While specific embodiments of the invention have been shown and described in detail to illustrate the application of the principles of the invention, it will be understood that the invention may be embodied otherwise without departing from such principles.

We claim:

1. A method for detecting the location of an edge of a workpiece, comprising:

positioning electromagnetic acoustic transducer (EMAT) sensor means at a known location adjacent the workpiece, using the EMAT sensor means to generate an ultrasonic wave along a surface of the workpiece toward the edge, and detecting a reflected ultrasonic wave from the edge;

measuring a round trip time-of-flight (TOF) of the ultrasonic wave to propagate from the EMAT sensor means to the edge, be reflected from the edge, and propagate back to the EMAT sensor means; and knowing a velocity of the ultrasonic wave in the workpiece, calculating the distance from the EMAT sensor means to the edge using the TOF and the velocity to determine the location of the edge on the workpiece as a function of the known location of the EMAT sensor means.

2. The method according to claim 1, comprising the step of positioning a pair of EMAT sensors spaced apart from one another and adjacent the workpiece, each EMAT sensor for generating an ultrasonic wave along a surface of the workpiece toward its respective edge of the workpiece and detecting a reflected ultrasonic wave from its respective edge.

3. The method according to claim 2, comprising the step of positioning the EMAT sensor means at a known location adjacent and above a surface of the workpiece.

4. The method according to claim 3, comprising the step of providing EMAT sensor means which each include separate mean; for transmitting and receiving ultrasonic waves.

5. The method according to claim 1, comprising the step of providing bi-directional EMAT sensor means for transmitting an ultrasonic wave to more than one edge of the workpiece and for receiving reflected ultrasonic waves from more than one edge of the workpiece, the distance to each edge being calculated as a function of the TOF from the bi-directional EMAT sensor means to each of the more than one edges.

6. The method according to claim 5, comprising the step of providing a bi-directional EMAT sensor means having separate means for transmitting and receiving ultrasonic waves.

7. The method according to claim 1, comprising the step of providing a pair of EMAT sensors at known locations with respect to a seam of the workpiece forming the edge to be located, transmitting ultrasonic waves from each EMAT sensor toward the seam and receiving reflected waves from the seam, and calculating the distance between each EMAT sensor and the seam as a function of the TOF of he transmitted and reflected wave and the velocity of the wave along the workpiece.

8. The method according to claim 1, comprising the step of generating ultrasonic surface waves in the workpiece.

9. The method according to claim 1, comprising the step of generating 90 degree shear waves in the workpiece.

10. A method for determining whether an edge of a workpiece is perpendicular to another line, comprising:

positioning electromagnetic acoustic transducer (EMAT) sensor means at a known location adjacent the workpiece and using the EMAT sensor means to generate an ultrasonic wave along a surface of the workpiece in a straight line of known orientation toward the edge;

measuring an amplitude of a received ultrasonic wave which has been reflected from the edge and received back at the EMAT sen or means while rotating the EMAT sensor means about a central axis of the EMAT sensor means; and determining at what angular position the maximum amplitude of the received ultrasonic wave that has been reflected from the edge is obtained, thereby indicating when the ultrasonic beam produced by the EMAT sensor means is perpendicular to the edge.

11. The method according to claim 10, comprising the step of generating ultrasonic surface waves in the workpiece.

12. The method according to claim 10, comprising the step of generating 90 degree shear horizontal waves in the workpiece.

* * * * *